United States Patent [19]
Church et al.

[11] Patent Number: 5,474,083
[45] Date of Patent: Dec. 12, 1995

[54] LIFTING MONITORING AND EXERCISE TRAINING SYSTEM

[75] Inventors: John Church, Miami; William R. Hassel, Davie; Fred Naghdi, Boca Raton, all of Fla.

[73] Assignee: Empi, Inc., St. Paul, Minn.

[21] Appl. No.: 152,082

[22] Filed: Nov. 15, 1993

Related U.S. Application Data

[63] Continuation of Ser. No. 657,954, Feb. 21, 1991, abandoned, which is a continuation of Ser. No. 319,850, Mar. 6, 1989, abandoned, which is a continuation of Ser. No. 938,830, Dec. 8, 1986, abandoned.

[51] Int. Cl.$^6$ ........................................... A61B 5/04
[52] U.S. Cl. ........................................... 128/733; 128/782
[58] Field of Search ........................... 128/733, 736, 128/774, 775, 781, 782; 340/573; 33/571, 512; 73/865.1

[56] References Cited

U.S. PATENT DOCUMENTS

| | | | |
|---|---|---|---|
| 3,875,929 | 3/1975 | Grant | 340/573 |
| 3,991,745 | 11/1976 | Yoslow et al. | 33/512 |
| 4,108,164 | 8/1978 | Hall, Sr. | 33/512 |
| 4,331,161 | 5/1982 | Patel | 128/736 |
| 4,367,752 | 1/1983 | Jimenez et al. | 128/782 |
| 4,399,824 | 8/1983 | Davidson | 128/736 |
| 4,418,337 | 11/1983 | Bader | 340/573 |
| 4,450,437 | 5/1984 | Ho | 340/573 |
| 4,655,227 | 4/1987 | Gracovetsky | 128/781 |
| 4,665,928 | 5/1987 | Linial et al. | 128/782 |
| 4,667,513 | 5/1987 | Konno | 128/774 |
| 4,667,685 | 5/1987 | Fine | 128/782 |

Primary Examiner—Kyle L. Howell
Assistant Examiner—John P. Lacyk
Attorney, Agent, or Firm—Kinney & Lange

[57] ABSTRACT

The invention is directed to a microprocessor based system utilizing electromyographic sensor to monitor muscle force for lift training and exercise training. In the lift training embodiment the electrodes of the electromyographic sensor are secured to a belt so that they are located adjacent to the lower back of the user when wearing the belt. The lift training embodiment is also provided with a goniometer to measure lifting angle during training, which together with muscle force generated by the lower back is compared in the microprocessor to a programmed lifting parameters and if these parameters are exceeded the user is warned by and audible indicator. The lift trainer embodiment also periodically measures interelectrode impedance to insure actual usage. The exercise training embodiment has a bar graph display displaying muscle intensity and two light emitting diodes alerting a user when to contract or relax a monitored muscle group. The microprocessor is programmed with a exercise routine and alerts a user when the routine is to begin, the duration of muscle contraction and relaxation, and the repetitions required. During exercise the user can monitor muscle intensity from the bar graph display and or auditory feedback element. An alternate lift training systems comprises a belt mounted goniometer which is operatively coupled to a microprocessor having an electronic memory for time logging a lifting session. To insure actual usage the belt is also provided with temperature and/or motion sensors.

18 Claims, 11 Drawing Sheets

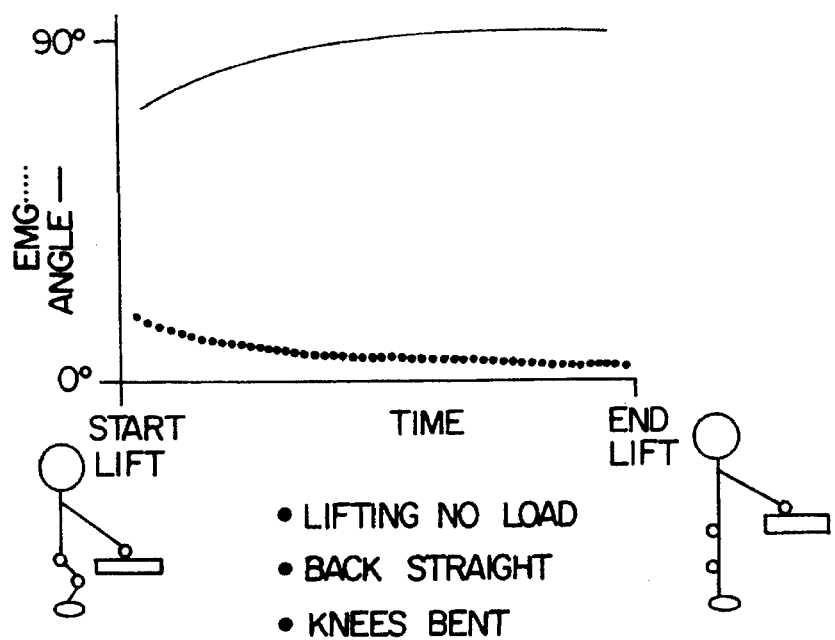
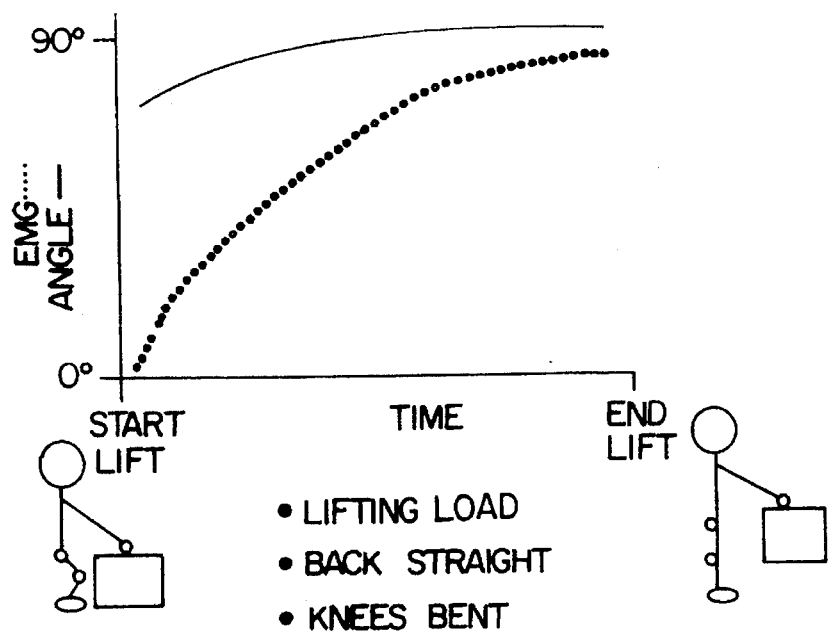

LIFTING MONITORING AND EXERCISE TRAINING SYSTEM

This application is a continuation of application Ser. No. 07/657,954, filed Feb. 21, 1991, now abandoned; which is a continuation of application Ser. No. 07/319,850, filed Mar. 6, 1989, now abandoned; which is a continuation of application Ser. No. 06/938,830, filed Dec. 8, 1986, now abandoned.

BACKGROUND OF THE INVENTION

1. Field of the Invention

The invention is directed to a system for monitoring the lifting motion and/or the exercise training of an individual. Both systems comprise a preprogrammed microprocessor that is operatively coupled to an electromyographic sensor that is used to measure muscle force for a predetermined muscle group. However an alternate embodiment of the lift training system, does not employ electromyographic sensors instead relying solely on a goniometer to monitor lifting angle.

2. Description of the Prior Art

Annually millions of workers suffer from work related low back pain, most of which is attributed to improper lifting techniques. Such injuries result in work time lost and disability claims costing employers large amounts of money each year.

A number of devices have been proposed to monitor and provide feedback as to a person's correct posture. Such devices may comprise longitudinal belts that are wrapped from a person's waist over his or her shoulder, these devices monitor belt tension insuring that the user's back is being held upright, See U.S. Pat. Nos. 3,608,541, 4,007,733, and 4,055,168. Other devices include conventional belts that are fitted with sensors for monitoring stomach sag, which indicates improper posture because of relaxation of the stomach muscles, See U.S. Pat. Nos. 3,582,935, and 3,670,320. U.S. Pat. No. 3,644,919, discloses a signaling device indicating the improper position of a skier's legs during skiing.

In addition to monitoring lifting technique and motion it is also important to monitor a person's exercise program during physical therapy to insure that the physical therapy is being done properly, for the correct intensity and duration. Devices for measuring overall physical loads have been proposed, See U.S. Pat. No. 4,394,865; but these devices do not tend to be directed to a specific muscle group for measuring the muscle force used in an exercise or the duration of that exercise.

SUMMARY

The amount of force exerted by a muscle is directly related to its enervation by virtue of the amplitude and frequency of constituent action potentials. Therefore it is possible to measure muscle force with electromyographic (EMG) techniques. In integrated electromyography (IEMG) the myoelectric signal is rectified and time averaged to produce an accurate representation of the EMG signal energy which can be related to muscle force.

In the lift monitoring mode of the present invention, an electromyographic sensor is secured to a belt that is wrapped around a user's waist so that electrodes of the sensor are positioned adjacent to the lower back muscles of the user's back. In this way the amount of muscle force exerted by the lower back muscles during a lifting operation can be monitored. It is also important to measure lumbar angle during a lifting operation to insure that heavy weights are lifted correctly, as such the belt is also provided with a goniometer for measuring lumbar angle during a lifting operation. Both the muscle force signal and the goniometer output are applied to a microprocessor which compares these signals with preprogrammed lifting parameters. If these signals exceed the preprogrammed lifting parameters an indicating means is activated to indicate to the user he has exceeded these parameters. An electronic memory is coupled to the microprocessor recording these events. The microprocessor can be coupled to a compliance computer which reads the memory and tabulates the lifting operations for evaluating various lifting operations and compliance with the preprogrammed parameters. The microprocessor and EMG sensor together with a signal source are used to measure interelectrode impedance to establish that the device is actually worn and used.

An alternate embodiment of this system comprises using a goniometer to measure lifting angle and logging into the memory of the microprocessor any time a user exceeds the lifting or lumbar angle parameters. The belt can also be fitted with temperature and/or motion sensors to monitor if the belt is being worn by a user.

A similar system is used in physical therapy wherein the therapist prescribes that a muscle or muscle group be isometrically exercised for a period of time during a specified time interval, such as a day. An electromyographic sensor is used to monitor IEMG and is coupled to a microprocessor which displays the IEMG intensity on a bar graph. The microprocessor is also provided with a clock which first indicates when an exercise program is to begin; second when to contract the muscle or muscle group; and third when to relax the muscle or muscle group. The microprocessor is also provided with an electronic memory for recording the actual time, duration of the tensioning, and the muscle force exerted. The microprocessor can be coupled to a compliance computer which reads the electronic memory and tabulates the exercise results, indicating compliance with predetermined exercise program.

The electrodes for the electromyographic sensor can be mounted in cotton gauze webbing that is the inner layer of a cast. In this way arm and leg muscles can be exercised and monitored while being encased in a cast. Additionally the electrodes can be mounted on cylindrical objects that can be fitted into natural body orifices for measuring muscle force exerted by the muscles attempting to close these orifices.

BRIEF DESCRIPTION OF THE DRAWINGS

FIGS. 5a–5d are graphs of muscles force and lifting angle versus time for various lifting scenarios.

FIG. 13 is an electrical block diagram of an alternate embodiment of the lift training system.

DETAILED DESCRIPTION

Figure 1:
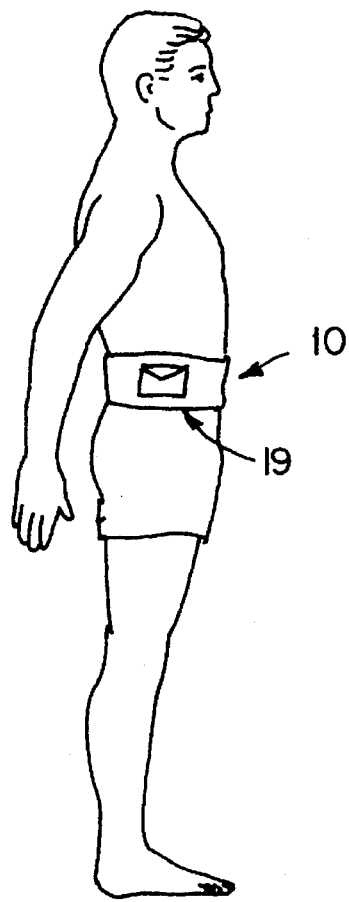
FIGS. 1 and 2 are perspective views of the lift training belt secured to a user.
Figure 2:
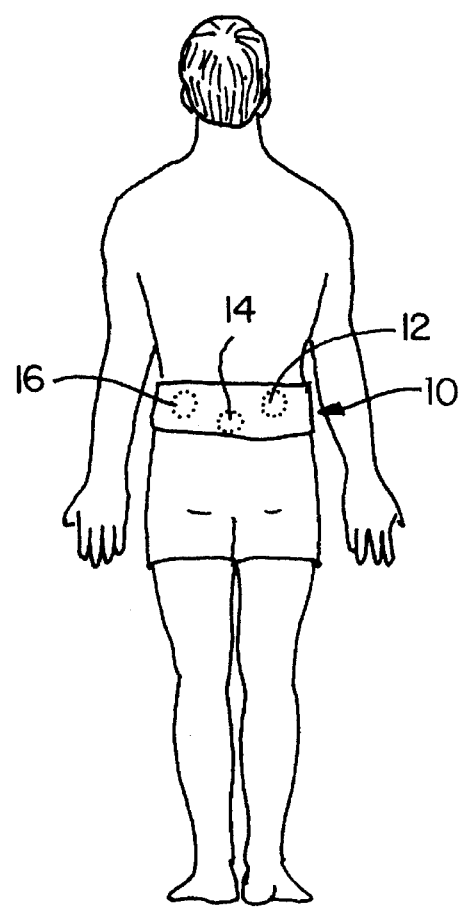
Figure 3:
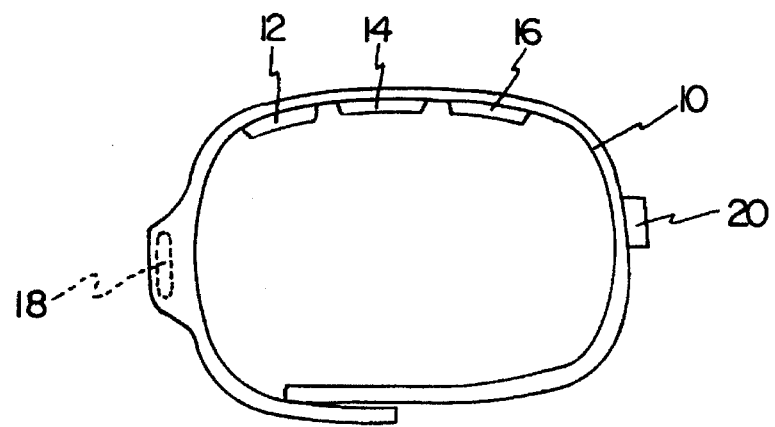
FIG. 3 is a top view of the belt.

FIGS. 1–3 illustrate the belt mounted lift training system. Belt 10 is secured to just above the waist of a user in a conventional manner. The belt is provided with three electrodes 12, 14 and 16 which are electrically coupled to monitoring device 18 through wires (not shown in these figures). The electrodes are secured to the belt so that as the belt is worn the electrodes are located adjacent to a patient's lower back. The training and monitoring device is located in a pocket on the belt. Goniometer 20 is also mounted on the belt and is located so that it is positioned adjacent to a patient's side so that as a patient bends the goniometer can monitor the bending angle. It should be noted that by mounting the training and monitoring device so that it too is located on the patent's side, the goniometer can be located in the device rather than having a separate mounting location on the belt.

The belt can be fabricated from a light weight elastomeric fabric and is designed to be worn just above the waist. The belt fastener or securing member can be made from hook and pile fasteners located at the adjoining ends of the belt. The electrodes themselves are silver element pads that serve as surface electrodes of an electromyographic sensor. The goniometer and the electrodes are connected to the monitoring device via wires located in the fabric that terminate in metallic snaps that can be coupled to mating snaps located in the training and monitoring device.

Figure 4:
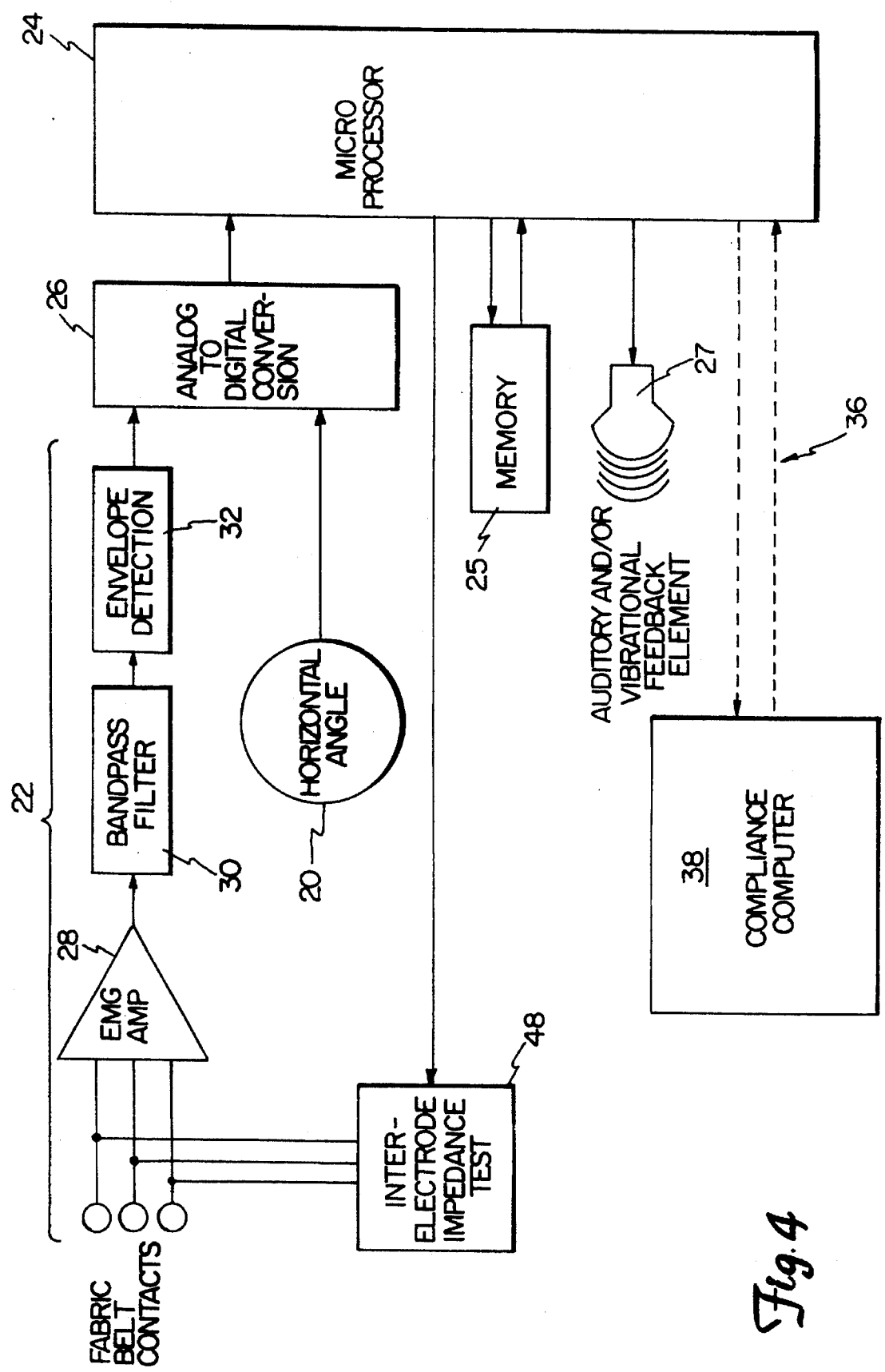
FIG. 4 is an electrical block diagram of the lift training system.

FIG. 4 is an electrical block diagram of the training and monitoring device. The monitoring device comprises electromyographic sensor 22 which is operatively connected to control means 24 through an analog to digital converter 26. Goniometer 20 is also coupled to the control means through converter 26. The control means comprises a microprocessor unit acting also as an internal clock and is interfaced to an electronic memory 25 that forms a recording means. The microprocessor is coupled to a indicator means 27, which can be auditory and/or vibrational for indicating to the user a lifting condition which exceeds preset parameters programmed into the microprocessor.

In operation the myoelectric signals from the three electrodes are amplified by high gain differential amplifier 28, filtered by bandpass filter 30 and directed to envelope detector 32 which converts the raw EMG waveform of the myoelectric signals into an approximation of the total myoelectric energy which essentially comprises a muscle force signal. Also, it is within the purview of the invention that at least one electromyographic sensor member may be disposed on the belt which senses muscle force and produces a rectified and time averaged signal forming a muscle force signal responsive to the lifting movement of the lower back of the user. As the resulting muscle force signal is an analog signal it is converted into a digital format acceptable to the microprocessor. Similarly the goniometer forms a horizontal angle signal that comprises a lifting angle signal that is also converted from an analog to a digitalformat before being directed to the microprocessor. It should be noted that goniometer measures the lumbar angle including bending or lifting angle components of anterior and/or left/right lateral angles.

FIG. 5 reflects the idealized behavior of lumbar angle and EMG measurement under several lifting conditions. The EMG curves shown do not not include components of intertia and body weight.

Figure 5C:
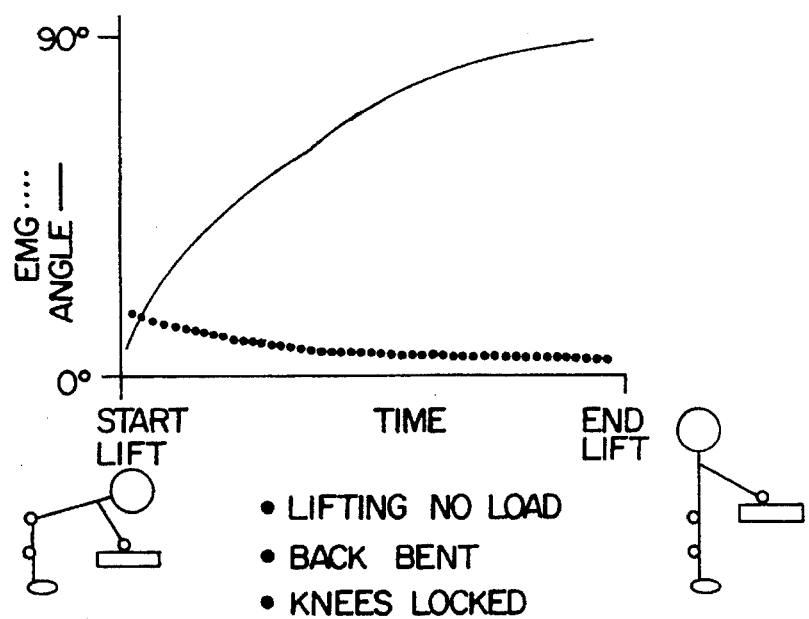
Figure 5D:
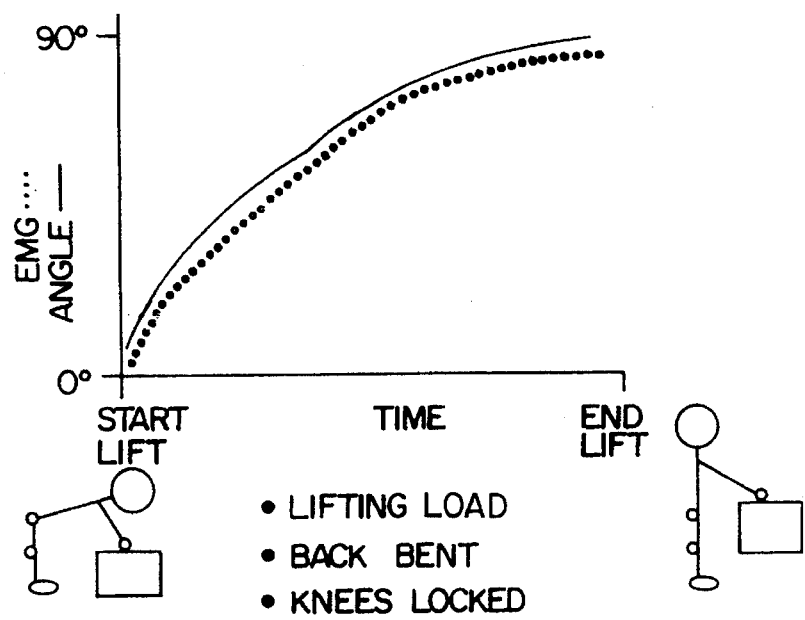

FIG. 5a and 5c are graphical presentations of lifting no loads in a back straight position and back bent position. As can be seen in the back straight position the horizontal angle changes only slightly whereas in the back bent position the horizontal angle changes from nearly zero degrees to ninety degrees. However since no additional load is involved in either lifting sequence the amount of muscle force (EMG) required is minimal. In FIGS. 5b and 5d a load is lifted and although the lifting angle is identical to the no load sequence, the amount of muscle force required in each sequence varies considerably because of the lifting methodology. In the back bent position the amount of muscle force required from the lower back tends to mirror the change in lifting angle where as in the back straight position during the initial lifting motion the amount of lower back muscle force is considerably reduced because the legs are doing the lifting.

In training a user of the system, a teacher programs the microprocessor via the compliance computer 38 with a set of lifting parameters which include limits as to muscle load and horizontal angle. As there is interplay between these parameters the teacher can set up a system wherein a combination of the parameters triggers a feedback warning signal. For example in FIGS. 5c the user has taken an incorrect lifting angle but since the user is not lifting any load the indicator is not triggered. However in FIG. 5d the user has taken an incorrect lifting position and is lifting a load, therefore the indicator is triggered. As such the present system gives the teacher the ability to program triggering parameters that are a combination of the lifting angle and muscle force required.

Figure 6:
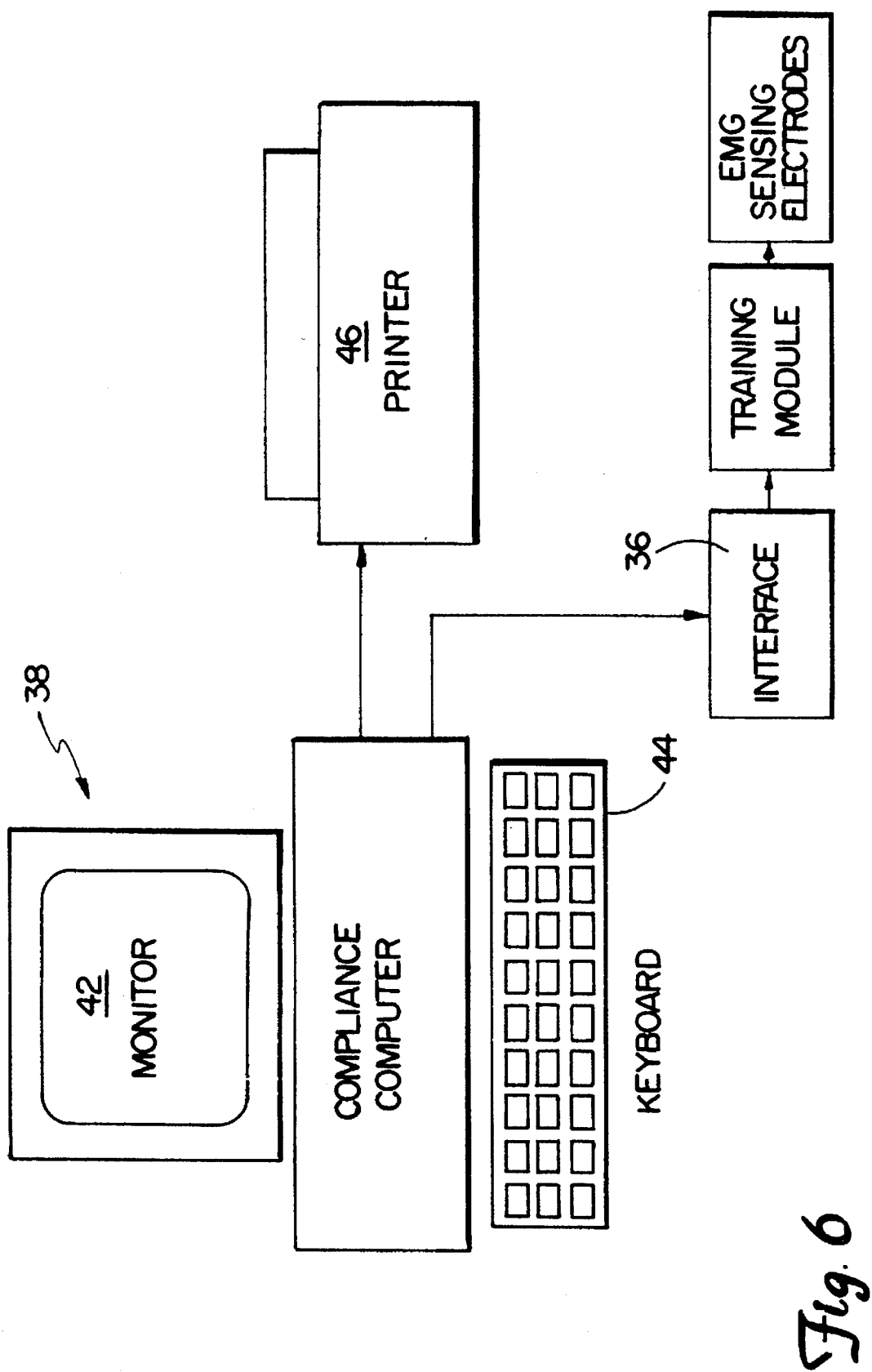
FIG. 6 is a block diagram of the lift training operating system.

The monitoring system is battery operated and located in a lockable housing so that after the teacher has programmed the microprocessor, the housing is locked and the battery cannot be tampered with by the user. The microprocessor is provided with interface 36 comprising a plug for coupling the microprocessor to compliance computer 38. The compliance computer can be an IBM PC compatible unit and is used to interrogate the memory so that a training session can be tabulated for evaluation by the teacher. In addition this interface can be used for programming the microprocessor with the programmed lifting parameters. As can be seen in FIG. 6, the compliance computer is provided with monitor 42, input keyboard 44, and printer 46.

Figure 8:
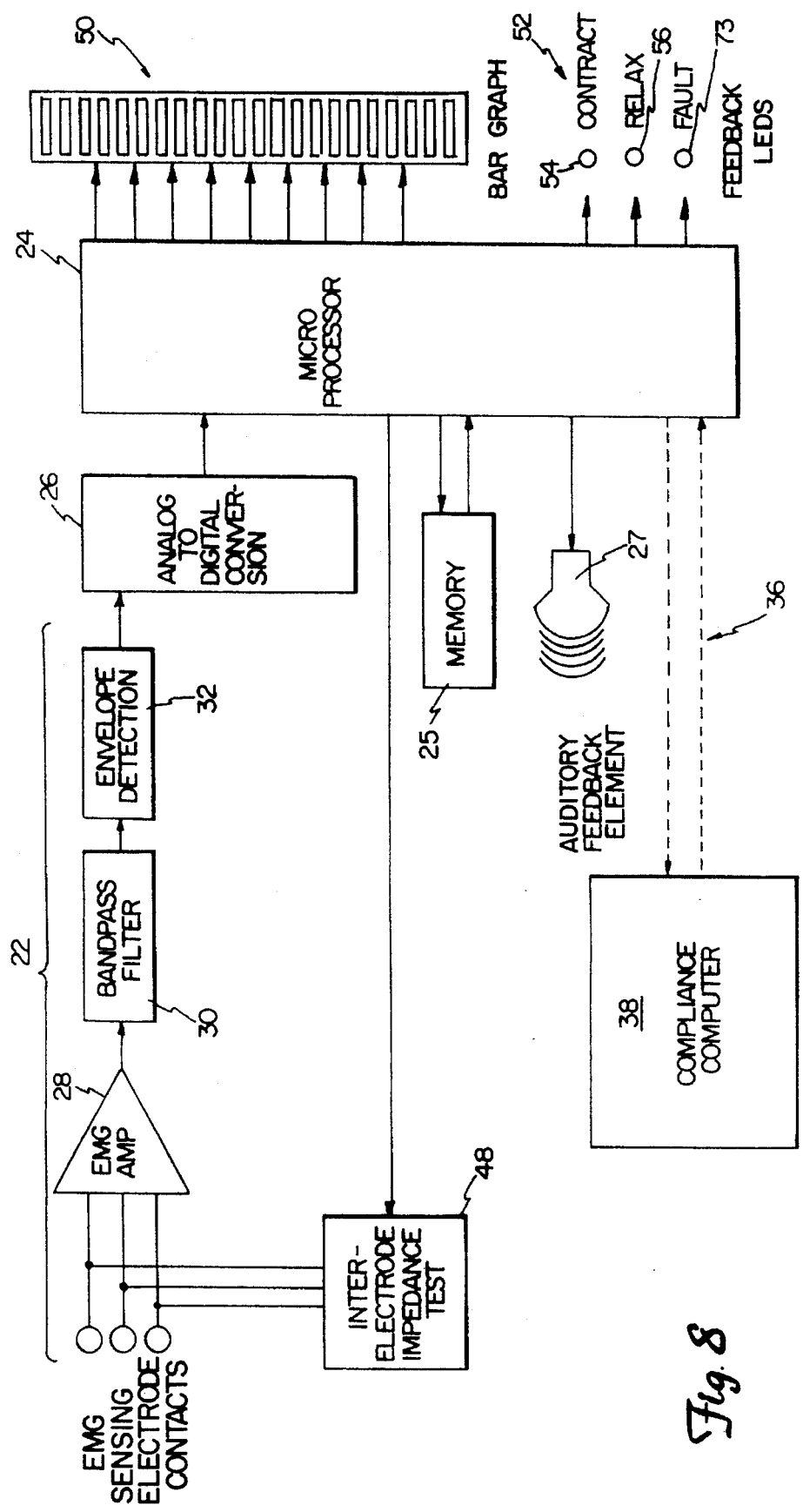
FIG. 8 is an electrical block diagram of the exercise training system.

To insure that the monitoring system is operating correctly the microprocessor periodically activates interelectrode impedance test 48 shown in FIG. 8 to check if electrode contact is sufficient. The test applies a bipolar sinusoidal signal across the EMG inputs, the impedance is then measured by the microprocessor. In addition the microprocessor can be provided with a testing system for testing battery voltage to insure proper voltage to the monitoring system. In the event that the contacts fail the impedance test or the battery has insufficient voltage the microprocessor signals the user through the indicator means and turns off the system.

FIGS. 7–12 are directed to an exercise training system which is similar to the lift training monitoring system. As can be seen in FIG. 8 the circuitry is similar except that the exercise training system is provided with visual feedback display means 50 comprising a bar graph, and alerting means 52 comprising three light emitting diodes. The auditory feedback element 27, which in the lifting training system is an indicating means, in this embodiment is used in conjunction with the visible display means and the alerting means to inform the patient audibly that these displays have been triggered.

Bar graph 50 is a liquid crystal or light emitting diodedisplay that is used for displaying muscle force used during use. The exercise training system is auto ranging with respect to the bar graph, the alogorithm for auto ranging the bar graph is disclosed in FIG. 9. During an exercise period light emitting diode 54 lights up indicating to the user to contract the muscle group that is equipped with the electromyographic electrodes. The user keeps that muscle contracted until light emitting diode 54 is turned off, and light emitting diode 56 lights up indicating to the user to relax the muscle group. Contract/relax cycles are repeated as determined by the preprogramed microprocessor. The intensity of the muscle contractions is fed back to the user by viewing bar graph 50 which indicates muscle force used.

A physical therapist first applies the electromyographic electrodes to a patient adjacent to the muscle group to be exercised. Then the therapist programs the microprocessor via the compliance computer of the training system, by programming a time interval in which the exercise routine is to begin, the timed interval for contracting a muscle group and relaxing a muscle group, and the number of repetitions. The therapist then couples the unit to the electrode leads and the patient can then conduct his own physical therapy by using isometric exercises for contracting the desired muscle group for the required duration and repetitions and monitoring the intensity of the exercise on the bar graph.

As with the lift training and monitoring system the exercise training system can be coupled to compliance computer 38 through interface 36, which can comprise a simple jack. The compliance computer is used to program the microprocessor and to tabulate the patient's performance with the exercise program by interrogating the electronic memory which recorded the exercise session. The therapist can then program into the microprocessor a new training routine based upon the patient's actual performance in the last training session. As with the lift training system the compliance computer is also used to program the microprocessor.

Figure 7:
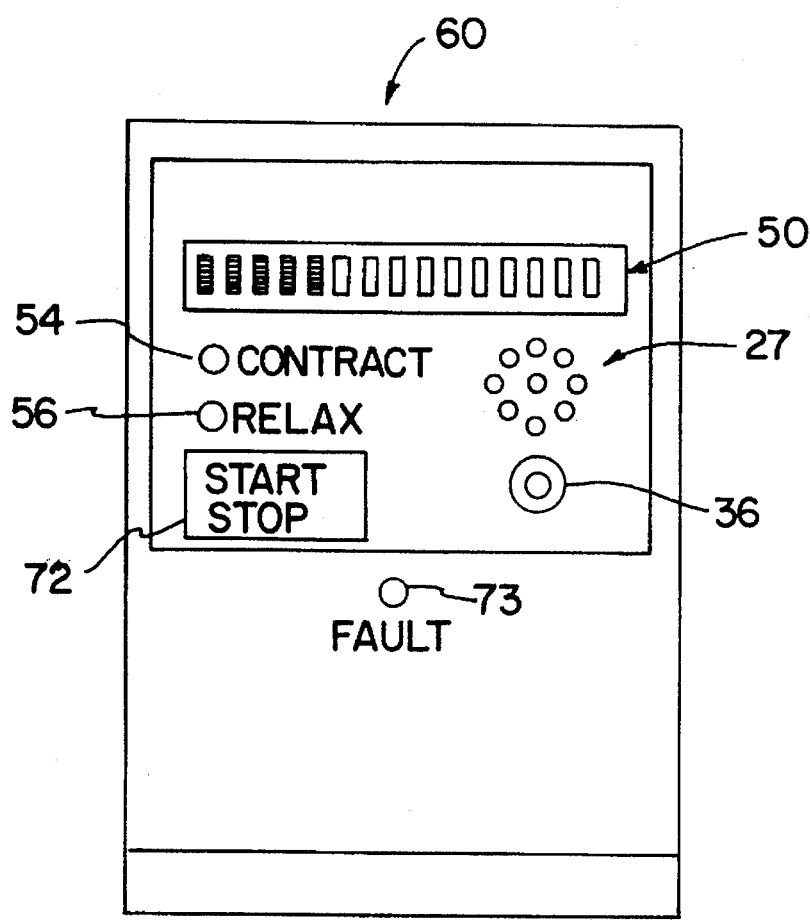
FIG. 7 is a front view of the exercise training device.

FIG. 7 is a front view of the training and monitoring device which is relatively compact. The circuitry including the microprocessor, the electronic memory, and the electromyographic processing circuitry are contained in housing 60. The device is provided with a start/stop switch 72 for overriding the exercise routine programmed into the microprocessor, and a third light emitting diode 73 indicates the device is not functioning correctly based upon its self testing, which is identical to the self testing of the lift training device.

Figure 9:
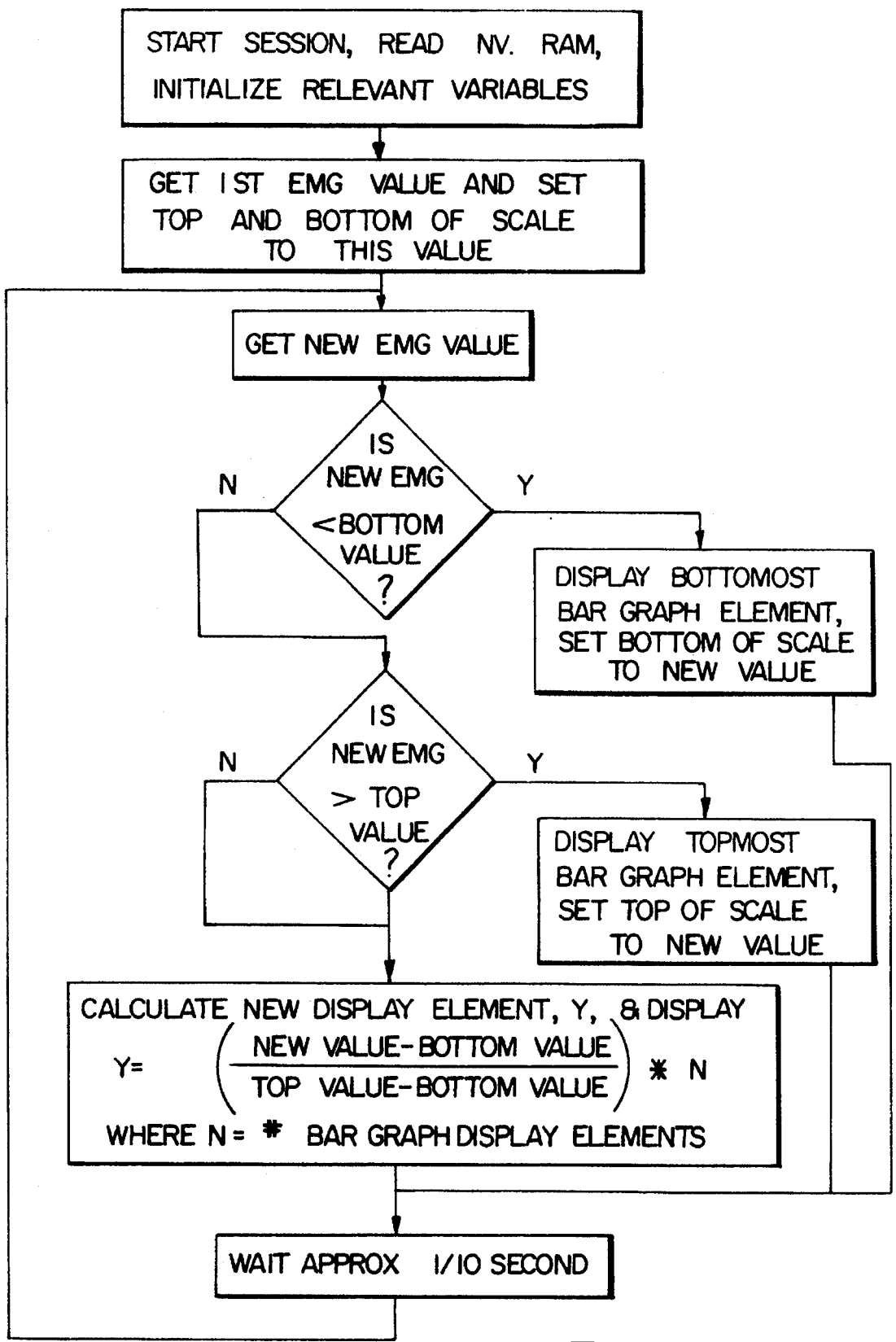
FIG. 9 is a flow chart of the auto ranging technique for the bar graph display of this exercise training system.

FIG. 9 discloses a flow chart illustrating the method of auto ranging the bar graph display. At the start of an exercise session the exercise parameters programed into electronic memory via the compliance computer are read by the microprocessor and are used to initialize relevant variables. The auto ranging method then through subsequent EMG (muscle force) readings sets a continually updated top value and bottom value for the bar graph scale. The method then calculates a new EMG reading located between the top and bottom value as a ratio of the EMG range and as such displays this ratio by lighting up the correct number of bar graph display elements.

Figure 10:
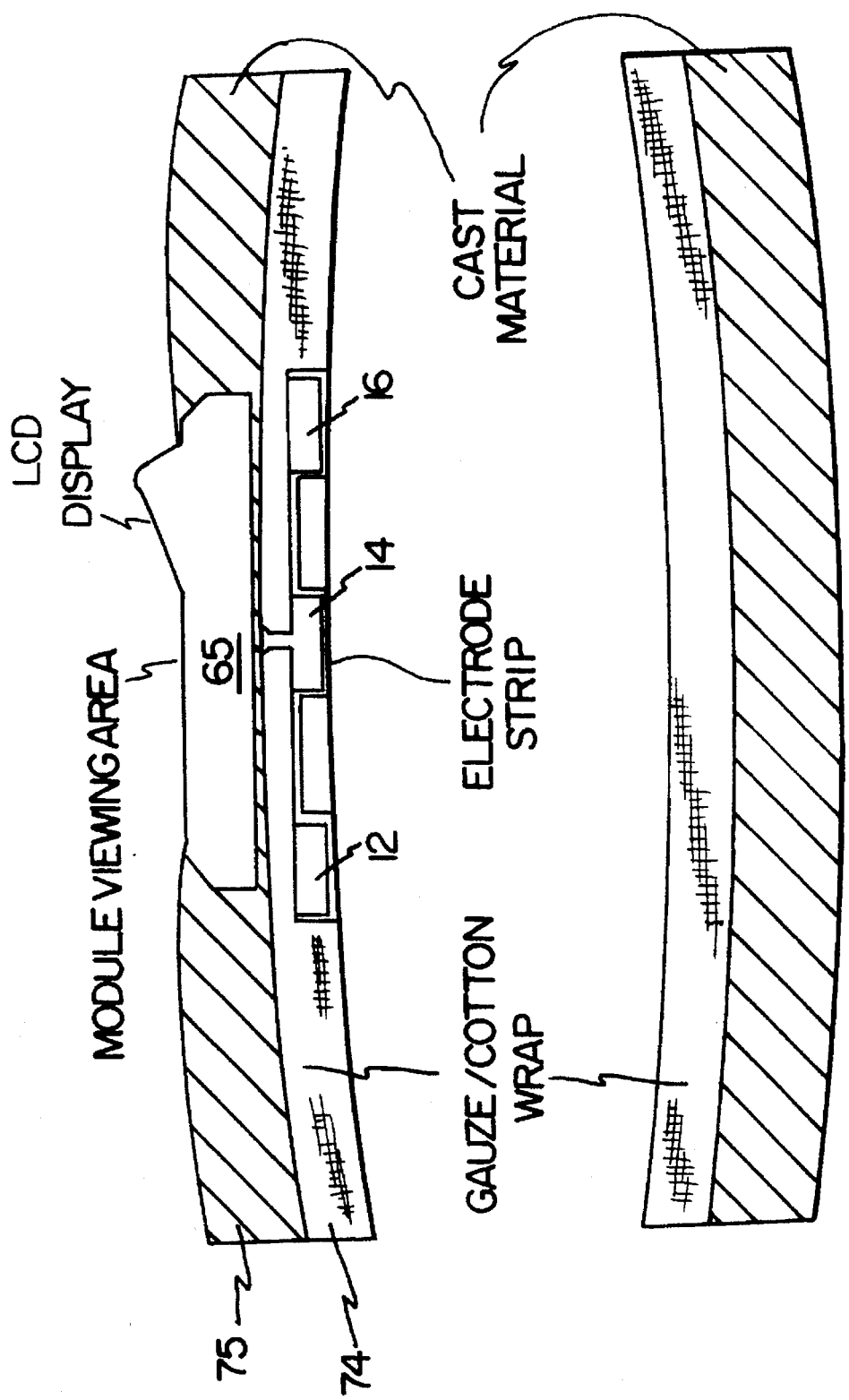
FIG. 10 is a cross sectional view of a cast using the exercise training electrodes.
Figure 11:
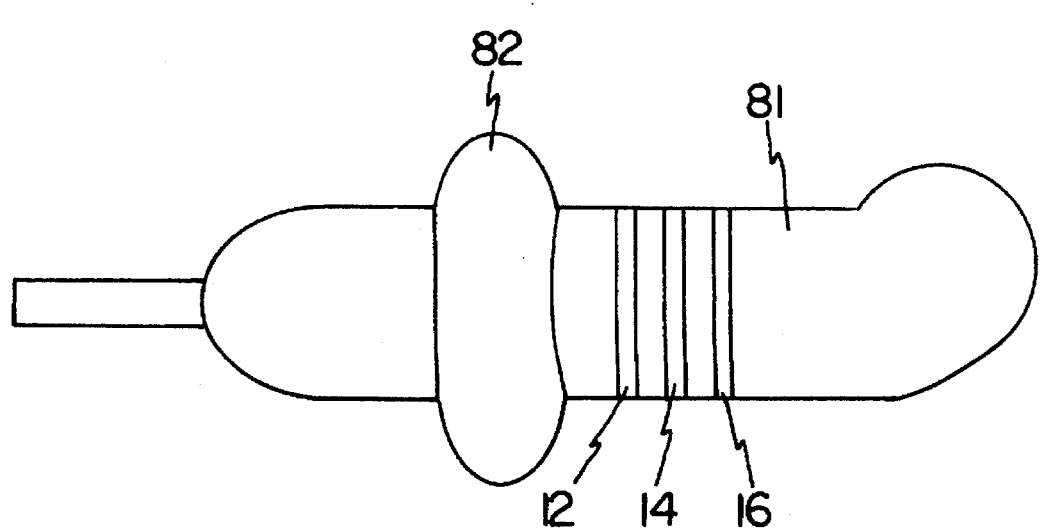
FIG. 11 is a side view of a cylindrical mounting assembly for the sensing electrodes that is adapted to be inserted into a female's vagina.
Figure 12:
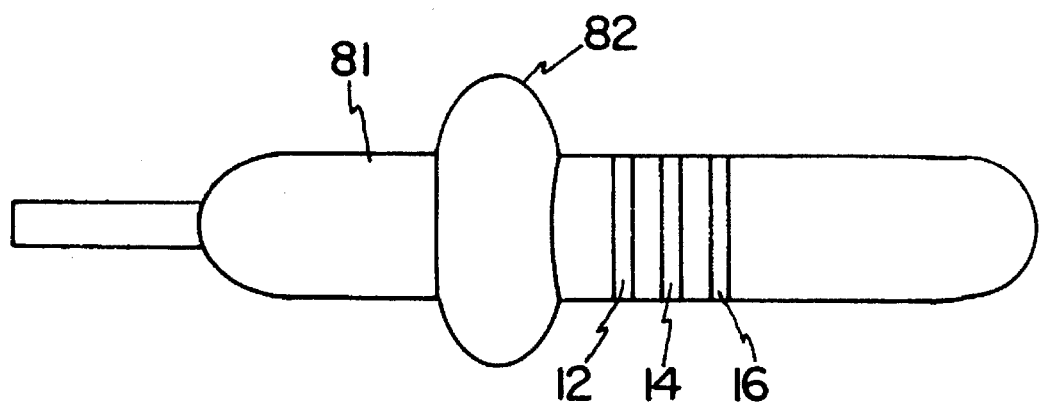
FIG. 12 is a side view of cylindrical mounting assembly for the sensing electrode that is adapted to be inserted into a user's anus.
Figure 19:
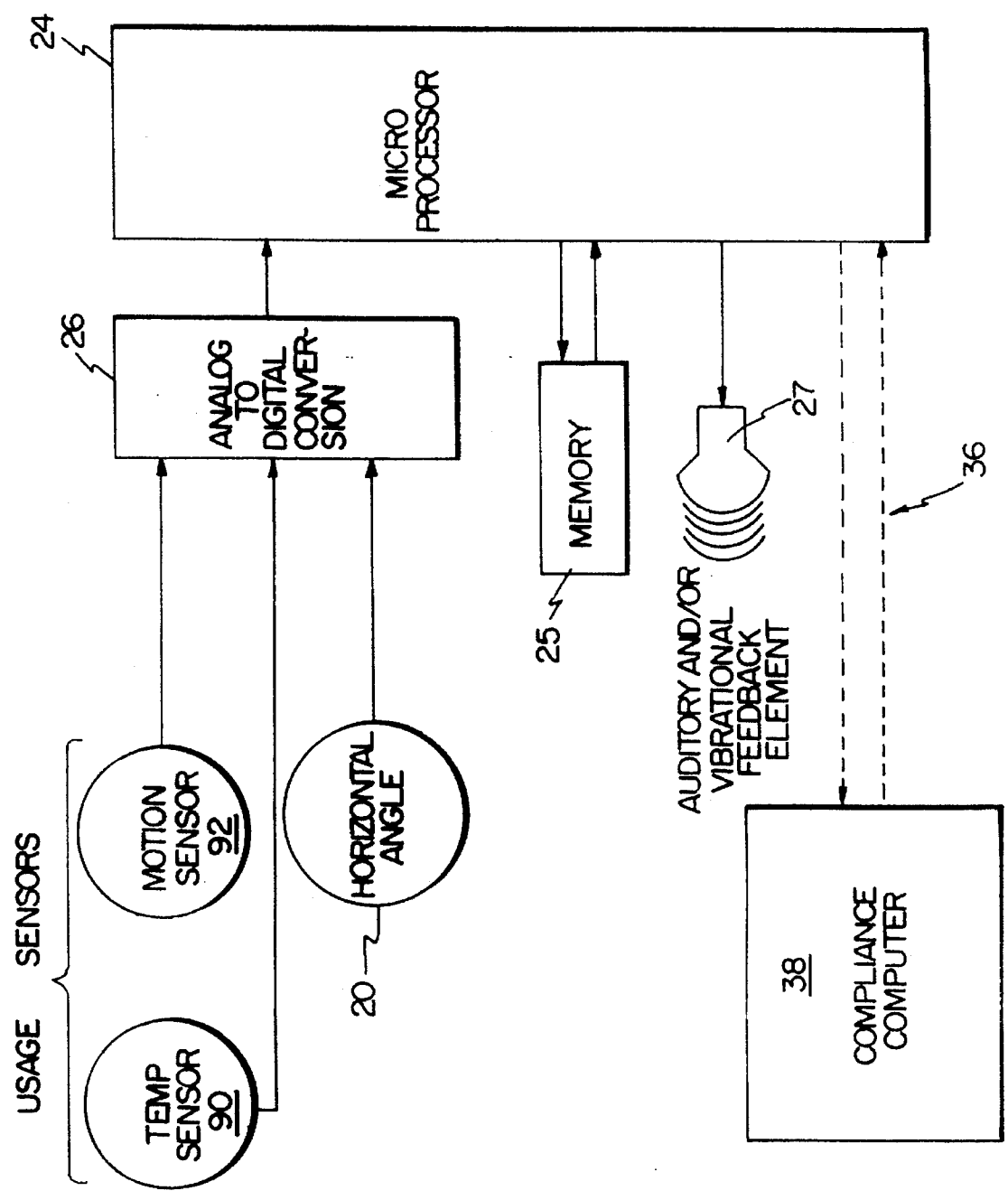

FIG. 10–12 disclose different devices for securing the electrodes of the electromyographic sensor to selected body location. In the embodiment illustrated in FIG. 10, the electrodes are secured to cotton gauze 74 that forms the inner liner of a cast for a limb. The monitoring housing and related circuitry because of its compact nature, can then be embedded in casting material 75 of the outer cast layer. The bar graph display is located at an angle to the housing to facilitate viewing by the patient.

FIGS. 11 and 12 are directed to electrode mounting assemblies that are designed to be inserted into a naturally occurring body orfices. These assemblies are cylindrical and have three stainless steel electrode bands located about their circumference. The embodiment illustrated in FIG. 11, comprises cylindrical member 80 which is inserted into a female vagina so that the female patient can monitor the exercise of associated vaginal muscles. The embodiment illustrated in FIG. 12 comprises cylindrical member 81 and is inserted into a patient's anus for monitoring a patient's exercise of the anal sphincter muscles. Both units are made from injected molded plastic, and are provided with depth gauges 82 which can be adjustable positioned and fixed on the cylindrical members by the therapist.

An alternate embodiment of the lift training system is illustrated in FIG. 13 and comprises a lift training system. Goniometer 20 which is used to measure lumbar angle. The temperature sensor 90 may be of the kind disclosed in Patel U.S. Pat. No. 4,331,161 or Davidson U.S. Pat. No. 4,399,824; the motion sensor 92 may be of the kind similarly used in odometers used by walkers, runners and athletes; and these temperature sensors and motion sensors are all deemed to be well known in the prior art. Temperature sensor 90 and/or motion sensor 92 are also mounted on the belt and indicate the belt is being worn by a user. In this way, the actual usage of the lift training system is logged together with a log of incorrect lifting angle.

As with the previously discussed lift training system, such as a device or component as the electromyographic sensor 22 of FIGS. 1–3, the microprocessor is programmed with lifting parameters via the compliance computer that when exceeded trigger indicator means 27 to alert the user. The compliance computer is used to interrogate the electronic memory for evaluating and tabulating the results of the lift monitoring session.

It should be noted that the ouput signals of usage sensors 90 and 92 do not have to be applied to converter 26 if the signals are already in digital form. In addition the usage sensors can be used on the belt disclosed in FIGS. 1–3.

The invention should not be limited to the above-described embodiments but should be limited solely to the claims that follows.

What is claimed and desired to be secured by letters Patent is:

1. A lifting monitoring system for providing information representative of a patient's lifting movements, including:

body mounting means adapted to releasably secure at least portions of the system to the patient's body;

EMG electrode means adapted to releasably attach to the patient's body, for sensing EMG signals representative of the patient's muscle activity during lifting movements;

lifting position sensing means mounted to the body mounting means, for providing position signals representative of the patient's body position during lifting movements;

memory means mounted to the body mounting means, for storing lifting data representative of predetermined standards of the patient's lifting movements as a function of muscle activity and body position;

control means mounted to the body mounting means and coupled to the EMG electrode means, the lifting position sensing means and the memory means, for generating alarm signals as a function of the EMG signals, position signals and lifting data when the patient's lifting movements exceed the predetermined standards; and alarm means mounted to the body mounting means and coupled to the control means, for providing sensory stimulus in response to the alarm signals.

2. The lifting monitoring system of claim 1 and further including means for mounting the EMG electrode means to the body mounting means.

3. The lifting monitoring system of claim 1 wherein the body mounting means includes a belt adapted to releasably secure around the waist of the patient.

4. The lifting monitoring system of claim 3 and further including means for mounting the EMG electrode means to the belt in such a manner that when the belt is worn by the patient, the electrode means are positioned adjacent to the patient's back to sense lower back muscle activity.

5. The lifting monitoring system of claim 4 wherein the EMG electrode means includes at least three electrodes.

6. The lifting monitoring system of claim 4 wherein the lifting position sensing means includes a goniometer mounted to the belt for providing position signals representative of the patient's back position during lifting movements.

7. The lifting monitoring system of claim 1 wherein:

the EMG electrode means includes means for sensing EMG signals representative of lower back muscle activity of the patient;

the lifting position sensing means includes means for sensing the lifting angle of the patient's back; and the memory means includes means for storing back lifting data representative of predetermined standards of the patient's lifting movements as a function of back muscle activity and back position; and the control means includes means for generating alarm signals as a function of the EMG signals, the lifting angle and lifting data when the patient's back lifting movements exceed the predetermined standards.

8. The lifting monitoring system of claim 1 wherein the control means further includes:

processing means for causing compliance data representative of the patient's lifting movements to be stored in the memory means; and interface means for outputting the compliance data from the memory means.

9. The lifting monitoring system of claim 8 and further including a compliance monitor interconnected to the interface means, for providing a display of the compliance data.

10. The lifting monitoring system of claim 1 and further including a programming source means for providing lifting data.

11. The lifting monitoring system of claim 10 wherein the control means further includes:

interface means configured for interconnection to the programming source means, for receiving lifting data; and processing means coupled to the interface means, for causing the received lifting data to be stored in the memory means.

12. A lifting monitoring system for providing information representative of a patient's lifting movements, including:

body mounting means adapted to releasably secure at least portions of the system to the patient's body;

EMG electrode means configured to be releasably attached to the patient's body, for sensing EMG signals representative of the patient's muscle activity during lifting movements;

lifting position sensing means mounted to the body mounting means, for providing position signals representative of the patient's body position during lifting movements;

memory means mounted to the body mounting means for storing compliance data representative of the patient's lifting movements;

control means mounted to the body mounting means and coupled to the EMG electrode means, the lifting position sensing means and the memory means, for causing the compliance data representative of the patient's lifting movements to be stored in the memory means as a function of the EMG signals and the position signals;

an interface means coupled to the control means for outputting the data.

13. The lifting monitoring system of claim 12 and further including a compliance monitor interconnected to the interface means, for providing a display of the compliance data.

14. The lifting monitoring system of claim 12 wherein the body mounting means includes a belt adapted to releasably secure around the waist of the patient.

15. The lifting monitoring system of claim 14 and further including means for mounting the EMG electrode means to the belt in such a manner that when the belt is worn by the patient the electrode means are positioned adjacent to the patient's back to sense lower back muscle activity.

16. The lifting monitoring system of claim 12 wherein:

the EMG electrode means includes means for sensing EMG signals representative of lower back muscle activity of the patient;

the lifting position sensing means includes means for sensing the lifting angle of the patient's back; and the control means includes means for causing compliance data representative of the patient's back lifting movements to be stored in the memory means.

17. A portable lifting monitoring system configured to be worn by a patient, for monitoring and providing feedback representative of a patient's lifting movements, including:

belt means adapted to releasably secure around the patient's waist;

EMG electrode means mounted to the belt means, for sensing EMG signals representative of the patient's back muscle activity during lifting movements;

goniometer means mounted to the belt means, for providing position signals representative of the patient's back position during lifting movements;

memory means mounted to the belt means, for storing back lifting data representative of predetermined standards of the patient's lifting movements as a function of back muscle activity and back position;

controller means mounted to the belt means and coupled to the EMG electrode means, the goniometer means and the memory means, for generating alarm signals as a function of the EMG signals, position signals and back lifting data when the patient's lifting movements exceed the predetermined standards; and alarm means mounted to the belt means and coupled to the control means, for providing sensory stimulus in response to the alarm signals.

18. A portable lifting monitoring system configured to be worn by a patient, for monitoring and providing information representative of a patient's lifting movements, including:

belt means adapted to releasably secure around the patient's waist;

EMG electrode means mounted to the belt means, for sensing EMG signals representative of the patient's back muscle activity during lifting movements;

goniometer means mounted to the belt means, for providing position signals representative to the patient's back position during lifting movements;

memory means mounted to the belt means for storing back lifting data;

controller means mounted to the belt means and coupled to the EMG electrode means, the goniometer means and the memory means, for causing the back lifting data to be stored in the memory means as a function of the EMG signals and position signals; and interface means coupled to the controller means and interconnected to a compliance monitor, for outputting the back lifting data.

\* \* \* \* \*